(12) United States Patent
Wang

(10) Patent No.: US 8,557,873 B2
(45) Date of Patent: Oct. 15, 2013

(54) METHOD FOR TREATING SEPTIC SHOCK OR ENDOTOXEMIA

(75) Inventor: Soo-Ray Wang, Taichung (TW)

(73) Assignee: Soo-Ray Wang, Taichung (TW)

( * ) Notice: Subject to any disclaimer, the term of this patent is extended or adjusted under 35 U.S.C. 154(b) by 417 days.

(21) Appl. No.: 12/815,182

(22) Filed: Jun. 14, 2010

(65) Prior Publication Data

US 2010/0317741 A1   Dec. 16, 2010

(30) Foreign Application Priority Data

Jun. 16, 2009   (TW) ................................ 98120028 A

(51) Int. Cl.
*A01N 33/02* (2006.01)
*A01N 33/18* (2006.01)
*A01N 33/24* (2006.01)
*A61K 31/13* (2006.01)
*A61K 31/04* (2006.01)

(52) U.S. Cl.
USPC .......................................... 514/663; 514/740

(58) Field of Classification Search
None
See application file for complete search history.

(56) References Cited

U.S. PATENT DOCUMENTS 6,011,066 A * 1/2000 Wang ............................ 514/561

OTHER PUBLICATIONS

Sennoun Nacira et al., Activated protein C improves lipopolysaccharide-induced cardiovascular dysfunction by decreasing tissular inflammation and oxidative stress, Crit Care Med 2009 vol. 37, No. 1, 246-255.
Gordon R. Bernard, M.D., et al., Efficacy and Safety of Recombinant Human Activated Protein C for Severe Sepsis, N Engl J Med, vol. 344, No. 10, Mar. 8, 2001, 699-709.

* cited by examiner

*Primary Examiner* — James D Anderson
*Assistant Examiner* — Stephanie Springer

(57) ABSTRACT

The invention provides a method for treating septic shock or endotoxemia, which comprises administering to a subject a therapeutically effective amount of a pharmaceutical composition comprising formula I, II, III or IV and their salt, ester or solvate thereof.

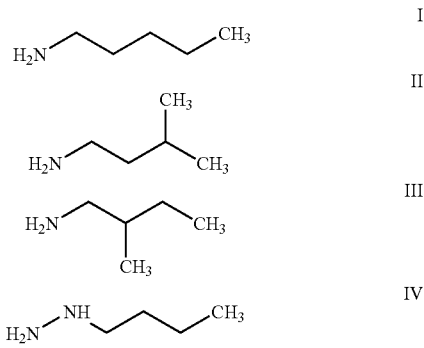

6 Claims, 1 Drawing Sheet

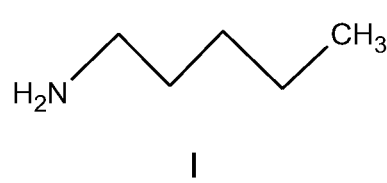
I
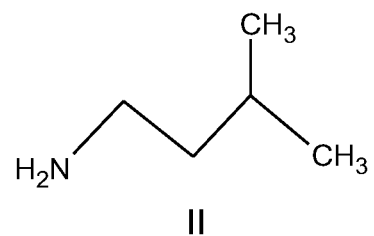
II
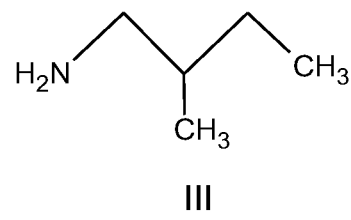
III
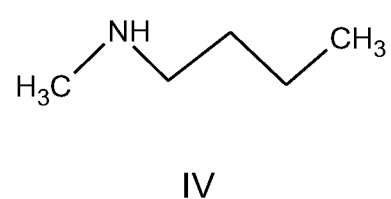
IV

METHOD FOR TREATING SEPTIC SHOCK OR ENDOTOXEMIA

FIELD OF THE INVENTION

The invention provides a method for treating septic shock or endotoxemia.

BACKGROUND OF THE INVENTION

Septic shock is a life-threatening complication of bacterial infection. Serious sepsis and septic shock are main reasons causing death in hospital infected patients. So called Sepsis means a whole-body inflammatory state (called a systemic inflammatory response syndrome, SIRS) and the presence of an obvious infection.

The main symptoms of septic shock include fever, cold dread, high respiratory rate and vague consciousness etc., which also include elevated or lowered body temperature (under 36° C. or over 38.3° C.), heart rate over 90 per minute, respiratory rate over 20 breaths per minute and white blood cell count over 12,000/cu.mm or less than 4,000/cu.mm.

The even worse situation may result in hypotension, hypoperfusion and multiple organ failure such as reduced urine flow (kidney failure), abnormal liver function and jaundice. This condition of vital organ dysfunctions due to insufficient irrigation of blood flow is called septic shock.

According to statistics, sepsis ICU death rate is about 30~50% and represents the 11th place of main death reason in U.S. Similarly, sepsis accounts for the 13th place of main death reason of Taiwan people according to the death reason statistical bulletin of the 90th year (2001) of the Republic Era generated by Taiwan Department of Health. Because sepsis has such a high incidence and mortality rates, how to treat the disease is always a tough problem to medical profession.

Septic shock is frequently complicated by the syndrome of disseminated intravascular coagulation (DIC) due to a massive activation of the coagulation system. While body itself also provides treatment for septic shock, many biological molecules are involved in anti-coagulation pathway.

In the case of bacterial infection, the host immune cells activation occurs with the release of cytokine and non-cytokine mediators, the most notorious of which are tumor necrosis factor-alpha (TNF-a), interleukin 1(IL-1) and interleukin 6 (IL-6). These factors are implicated in the diffuse activation of a systematic inflammatory response. As a result, mediators with vasodilatory and endotoxic properties are release systematically, including prostaglandins, thromboxane A2 and nitric acid. This results in vasodilatation and endothelial damage, which lead to hypotension and capillary leak. In addition, cytokine activates the coagulation pathway, resulting in capillary microthrombi and end-organ ischemia.

There have been researches of several targets for septic shock treatment, comprising steroid, recombinant APC and many chemical compounds.

Protein C is a major anti-coagulation component which functions as vitamin K-dependent serine protease enzyme and can be cleaved by coagulation factor V and VIII into activated form. Protein S functions as a cofactor to Protein C in the inactivation of coagulation factors V and VIII. Protein C is activated in a sequence that starts with Protein C and thrombin binding to a cell surface protein thrombomodulin. The activated protein C (APC), along with protein S and a phospholipid as cofactors, degrades coagulation factor V and VIII, thus inhibit body from coagulation.

According to Bernard G R et al., 2001, recombinant human activated protein C has anti-thrombotic, anti-inflammatory and profibrinolytic properties. Based on the earlier reports, it is known that activated protein C can protect animal and human from septic shock. However, the effects of APC have remained to be discovered. Nacira S had demonstrated the protective effect of activated protein C, prevented the reduction of blood pressure induced by LPS and improved both vascular hyperactivity and myocardial performance, in rats. This effect was associated with decreased up-regulation of NF-kappaB, iNOS and MMP-9 (Nacira S et al., Crit. Care Med. 2009 January; 37(1):246-55). Although it was effective, a large randomized clinical trials demonstrated only a 6.1% absolute decrease in mortality among patients with severe sepsis, while side effect along with efficacy exists. (Bernard G. R. et al., N Engl J Med 2001, 8; 344(10):699-709).

Besides, U.S. Pat. No. 4,388,318 disclosed a method of treating endotoxin shock with a pyrimido-pyrimidine derivative. Since E. coli endotoxin may exert its hypotensive effect by activating automatic blood pressure regulatory circuit in central nervous system, the administrating of a pyrimido-pyrimidine derivative will have hypertensive effect acting on the medullary cardiovascular regulatory system.

U.S. Pat. No. 6,011,066 disclosed an amine compound of chemical formula $C_2H_2R1R2R3NH_2$ for treating septic shock and a chemical structure thereof, wherein R1 and R2 are chosen from hydrogen, hydrocarbon, carboxyl group, amine group or alkyl group containing 1~8 carbons, and R3 is chosen from hydrogen, hydrocarbon, carboxyl group, phenyl group and its substitution, acrylamine, alkylamine containing 3~8 carbons, alkylamino-carboxylic acid or an effective amount of their salt, ester or solvate thereof. The amine compound was administrated to a subject orally or parenterally.

Among these researches, steroid has been regarded as the drug of choice to combat inflammation for a long time. But how much will be an effective dosage to treat sepsis and how long the treatment should be taken (if it did not cause side effects) have been plagued by the medical profession.

Therefore, a composition or a treating method having more effective bioactivity is demanded for reducing the mortality of sepsis and sepsis shock.

BRIEF DESCRIPTION OF THE DRAWINGS

FIG. 1 illustrates the chemical formulas of the medical composition of the present invention, where I is amylamine, II is isoamylamine, III is 2-methylbutamine and IV is n-methylbutamine.

SUMMARY OF THE INVENTION

The present invention discloses a method for treating septic shock or endotoxemia, which comprises administering to a subject a therapeutically effective amount of an active pharmaceutical composition comprising compounds with formula I, II, III or VI and their salt, ester or solvate thereof, wherein compound I, II, III and VI are represented by SS1, SS2, SS3 and SS9.

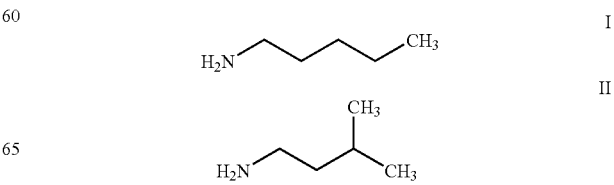

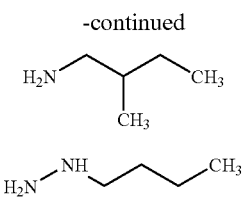

DETAILED DESCRIPTION OF THE INVENTION

The present invention discloses a method for treating septic shock or endotoxemia which comprises administering to a subject a therapeutically effective amount of a pharmaceutical composition comprising formula I, II, III and IV as its parent form, and their salt, ester or solvate thereof, where I is amylamine, II is isoamylamine, III is 2-methylbutamine and IV is n-methylbutamine. Compound I, II, III and IV are represented by SS1, SS2, SS3 and SS9.

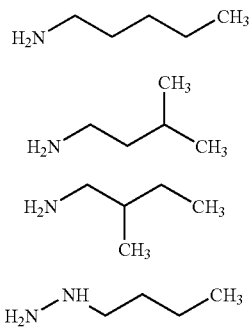

In a better embodiment, the pharmaceutical composition further includes a pharmaceutical acceptable carrier such as phosphate buffer solution.

According to the present invention, the pharmaceutical composition can be administrated parenterally, for example, in sterile liquid dose form and intraperitoneally injected to the subject. The pharmaceutical composition can also be administrated orally, for example in sterile liquid dose forms such as syrup and suspension, or in solid dosage forms such as capsules, tables and powder.

The subject in the present invention is mammal. In an embodiment, the subject is mice. In another embodiment, the subject is human.

In the present invention, a therapeutically-effective pharmaceutical composition represents what amount is sufficient to reduce, inhibit, or prevent shock induced by endotoxins or bacteremia in an individual.

Please refer to the following pictures and examples. It is noted that the following examples are presented herein to describe the best mode of the present invention, while they are not intended to limit the present invention.

Example 1

Experimental Materials

The mice used in this invention were male balb/c having body weights around 20 g, five to six weeks old. Each mouse was intraperitoneally injected with *E. coli* lipopolysacharide (LPS) 0.4 mg in 1 ml sterile saline. After 30 minutes, each mouse was intraperitoneally injected with one of the following compounds: amylamine, isoamylamine, 2-methylbutamine, n-methylbutamine. The above compounds were dissolved in 1 ml sterile saline to be pH 7.4. The *E. coli* LPS was serotype 0111:B4 obtained from Sigma (St. Louis, Mo.). The survival rates were observed for three days.

Example 2

Therapeutic Effect of Different Compounds (1) Amylamine

TABLE 1

| SS1 Conc.* (%) | 0 | 0.1 | 0.3 |
|---|---|---|---|
| Survival/total mice | 2/17 | 3/17 | 9/17 |
| Survival rate (%) | 12 | 18 | 53 |
| $X^2$ | | | 6.585 |
| P-value# | | NS** | 0.026 |

*The concentration in 1 ml administered to mice
Statistic test analyzed by the test of contingency table
**Nonsense value of statistics Each mouse was intraperitoneally injected with *E. coli* lipopolysaccharide (LPS) 0.4 mg in 1 ml saline, and was then injected with 1 ml amylamine (represented by SS1) of different concentrations (0%, 0.1%, and 0.3%) 30 minutes later. The survival rates of mice were observed for three days. The results presented in Table 1 show that 0.3% of amylamine has the best therapeutic effect, and the significant P value is 0.026. The therapeutic effect goes down if the dose above 0.3%. The best treatment volume of amylamine is 0.15 ml/Kg body weight of the mouse.

(2) Isoamylamine

Each mouse was intraperitoneally injected with *E. coli* lipopolysacharide (LPS) 0.4 mg in 1 ml saline, and then injected with 1 ml isoamylamine (represented by SS2) of different concentrations (0%, 0.1%, and 0.3%) 30 minutes later. The survival rates of mice were observed for three days. The results presented in Table 2 shows that 0.1% of isoamylamine has the best therapeutic effect, and the significant P value is 0.001. The therapeutic effect goes down if the dose above 0.1%. The best treatment volume of isoamylamine is 0.05 ml/kg body weight of the mouse.

TABLE 2

| SS2 Conc.* (%) | 0 | 0.1% | 0.3% |
|---|---|---|---|
| Survival/total mice | 3/18 | 15/18 | 9/18 |
| Survival rate (%) | 17 | 83 | 50 |
| $X^2$ | | 16 | 4.5 |
| P-value# | | 0.001 | 0.075 (NS**) |

*The concentration in 1 ml administered to mice
Statistic test analyzed by the test of contingency table
**Nonsense value of statistics (3) 2-methylbutamine Each mouse was intraperitoneally injected with *E. coli* lipopolysacharide (LPS) 0.4 mg in 1 ml saline, and then injected with 1 ml 2-methylbutamine (represented by SS3) of different concentrations (0%, 0.1%, and 0.3%) 30 minutes later. The survival rates of mice were observed for three days. The results presented in Table 3 show that 0.1% of 2-methylbutamine has the best therapeutic effect, and the significant P value is 0.002. The therapeutic effect goes down if the dose above 0.1%. The best treatment volume of 2-methylbutamine is 0.05 ml/kg body weight of the mouse.

TABLE 3

| SS3 Conc.* (%) | 0 | 0.1% | 0.3 |
|---|---|---|---|
| Survival/total mice | 4/30 | 16/30 | 10/30 |
| Survival rate (%) | 13 | 53 | 33 |
| $X^2$ | | 10.8 | |
| P-value# | | 0.002 | NS** |

*The concentration in 1 ml administered to mice
Statistic test analyzed by the test of contingency table
**Nonsense value of statistics (4) N-methylbutamine Each mouse was intraperitoneally injected with *E. coli* lipopolysacharide (LPS) 0.4 mg in 1 ml saline, and then 30 minutes later injected with 1 ml n-methylbutamine (represented by SS9) of different concentrations (0%, 0.1%, 0.3% and 1.0%) 30 minutes later. The survival rates of mice were observed for three days. The results presented in Table 4 show that 1.0% of n-methylbutamine has the best therapeutic effect, and the significant P value is 0.04. The therapeutic effect goes down if the dose above 1.0%. The best treatment volume of n-methylbutamine is 0.5 ml/kg body weight of the mouse. The dose of SS9 above 1.0% is toxic to mouse.

TABLE 4

| SS9 Conc.* (%) | 0 | 0.1 | 0.3 | 1.0 |
|---|---|---|---|---|
| Survival/total mice | 2/13 | 5/13 | 7/13 | 8/13 |
| Survival rate (%) | 15 | 39 | 54 | 62 |
| $X^2$ | | | 4.25 | 5.85 |
| P-value# | | NS** | 0.10 | 0.04 |

*The concentration in 1 ml administered to mice
Statistic test analyzed by the test of contingency table
**Nonsense value of statistics According to the above results, injecting solution containing 0.1% isomethylamine (SS2) has the best therapeutic effect, and the significant P value is 0.001. SS2 has a more significant therapeutic effect comparing to the other three compounds SS1, SS3 and SS9, while therapeutic effects of the four compounds achieve the statistic significance as well.

In addition, comparing the results of the present invention to Bernard's research in 2001, the four compounds SS1, SS2, SS3 and SS9 have a higher therapeutic effects and decreased mortality over recombinant APC, and are more easily for drug delivery and manufacture, which is an important feature considered in medical use.

The description above should not be constructed as limiting the scope of the present invention. For example, the combination of any two compounds selected from SS1, SS2, SS3 and SS9 will provide therapeutic effect for septic shock, and the skilled person may deduce that the combination of any three or four compounds will result in significant therapeutic effect for septic shock. Chemical mixtures of the compounds, such as their salt, ester or solvate will also be considered the target for sepsis treatment derived from the present invention. Therefore, the scope of the invention should be determined by the appended claims and their legal equivalents, rather than by the example given.

What is claimed is:

1. A method for treating septic shock or endotoxemia, which comprises administering to a subject afflicted with septic shock or endotoxemia a therapeutically effective amount of pharmaceutical composition comprising formula I as its parent form, and its salt or solvate thereof

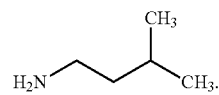

2. The method according to claim 1, wherein the pharmaceutical composition further comprises a pharmaceutically acceptable carrier.

3. The method according to claim 2, wherein the carrier comprises phosphate buffer.

4. The method according to claim 1, wherein the pharmaceutical composition is administered orally or parenterally.

5. The method according to claim 1, wherein the subject is a mammal.

6. The method according to claim 5, wherein the subject is human.

* * * * *